United States Patent
Geiger et al.

(10) Patent No.: US 9,090,384 B2
(45) Date of Patent: Jul. 28, 2015

(54) INSERT FOR A TUBE FOR DISPENSING LIQUID CONTENT AND TUBE WITH SUCH AN INSERT

(75) Inventors: Andreas Geiger, Steffisburg (CH); Christian Kubesch, Oberdiessbach (CH); Jan Mathys, Oberdiessbach (CH)

(73) Assignee: Hoffmann Neopac AG, Thun (CH)

( * ) Notice: Subject to any disclaimer, the term of this patent is extended or adjusted under 35 U.S.C. 154(b) by 0 days.

(21) Appl. No.: 14/359,955

(22) PCT Filed: Nov. 25, 2011

(86) PCT No.: PCT/CH2011/000287
§ 371 (c)(1),
(2), (4) Date: May 22, 2014

(87) PCT Pub. No.: WO2013/075256
PCT Pub. Date: May 30, 2013

(65) Prior Publication Data
US 2014/0332567 A1    Nov. 13, 2014

(51) Int. Cl.
*B65D 47/18* (2006.01)
*A61F 9/00* (2006.01)

(52) U.S. Cl.
CPC .............. *B65D 47/18* (2013.01); *A61F 9/0008* (2013.01)

(58) Field of Classification Search
CPC .............................. B65D 47/18; A61F 9/0008
USPC ................................................. 222/420, 421
See application file for complete search history.

(56) References Cited

U.S. PATENT DOCUMENTS

| | | | |
|---|---|---|---|
| 1,431,060 A * | 10/1922 | Tabor | 49/256 |
| 2,576,403 A | 11/1951 | Kirschenbaum | |
| 2,811,283 A | 10/1957 | Bowen | |
| 3,102,651 A * | 9/1963 | Boese | 215/43 |
| 4,936,498 A * | 6/1990 | Pirila | 222/420 |
| 7,832,594 B2 * | 11/2010 | Yamada et al. | 222/189.06 |
| 2011/0125111 A1 * | 5/2011 | Chibret et al. | 604/300 |

FOREIGN PATENT DOCUMENTS

| | | |
|---|---|---|
| DE | 649049 | 8/1937 |
| WO | 0169679 A1 | 9/2001 |
| WO | WO 2004069679 A1 * | 8/2004 |

OTHER PUBLICATIONS

International search report corresponding to PCT/CH2011/000287 dated Jul. 16, 2012.

* cited by examiner

*Primary Examiner* — Daniel R Shearer
(74) *Attorney, Agent, or Firm* — McCormick, Paulding & Huber LLP

(57) ABSTRACT

The present invention relates to an insert (5) for a tube (1) for dispensing liquid content in the form of drops, wherein the insert (5) comprises at least one notch (16; 17) at its outer wall, with the notch (16; 17) extending in the longitudinal direction, wherein the insert (5) is provided with an annular indentation (10), the annular indentation (10) dividing the insert into a proximal part (7) and a distal part (8) that are connected by a shaft (9), wherein both the proximal part (7) and the distal part (8) comprise a notch (16; 18) extending in the longitudinal direction on the respective outer wall, and wherein the outer diameter of the proximal part (7) and the outer diameter of the distal part (8) of the insert (5) are such that they match the inner diameter of a spout (2) of a tube (1), into which the insert (5) shall be placed. The invention further relates to a tube (1) with such an insert (5).

12 Claims, 3 Drawing Sheets

INSERT FOR A TUBE FOR DISPENSING LIQUID CONTENT AND TUBE WITH SUCH AN INSERT

CROSS REFERENCE TO RELATED APPLICATIONS

This application claims the priority of PCT Application No. PCT/CH2011/000287, filed on Nov. 25, 2011, the disclosure of which is incorporated herein by reference in its entirety.

TECHNICAL FIELD

The invention relates to an insert for a tube for dispensing liquid content in the form of drops and to a tube with such an insert. Typical application areas are among others in pharmaceutics and cosmetics. The insert and the tube are especially suitable for dispensing viscose liquids.

BACKGROUND

With conventional tubes it is often not possible to dispense liquids in the form of drops, even if the liquids are principally able to form drops. Instead the liquid is often dispensed in the form of a jet or spurt, which makes precise dosing of the liquid difficult. With some conventional tubes drop-dispensing might be possible, if a user only applies very light pressure to the tube body, which, however, can impair ease of application and user-friendliness.

As an alternative to tubes, bottles with a drop dispenser are known for dispensing liquids in the form of drops. The drop dispensers comprise a longitudinal delivery channel with an opening, through which the liquid is dispensed, with the delivery channel typically having a length that lies in the range below 1 mm and the opening typically having a diameter of up to 0.1 mm. With this rather small diameter of the opening and the rather large length of the delivery channel only a limited decrease in pressure can be achieved. With conventional drop-dispensing bottles the size of the drops thus generally depends on the user. When the user exerts a larger pressure onto the interior of the bottle, i.e. by more intense tapping on the bottom of the bottle, the liquid will trail after faster through the delivery channel, such that each drop can be fed with more liquid before it breaks away/drops from the opening of the delivery channel.

Drop-dispensing tubes are often provided with drop dispensers that consist of two elements and that are mounted onto the proximal end of the tube body from above, the proximal end of the tube body being the end from which the liquid passes into the spout. This kind of drop-dispensing tubes has interfaces between the two elements of the drop dispenser and between the drop dispenser and the inner wall of the tube spout, which interfaces must be sealing surfaces. The sealing surfaces must be dimensioned highly accurately, in particular in relation to each other. Furthermore, usually the materials of the sprout, of the elements of the drop dispenser, of the tube shoulder and of the tube body must follow a certain sequence regarding varying degrees of hardness to allow for the functioning of the drop-dispensing tube. The same material can, for example, not be used for the drop dispenser that is used for the tube shoulder. These requirements regarding the varying degrees of material hardness put a further burden on logistics and governmental approval of this kind of drop-dispensing tubes when employed for administering pharmaceutical products. Furthermore, with this kind of drop-dispensing tubes administration of liquids of high viscosity such as oils, serums, and emulsions is difficult as these liquids may more easily lead to leakage due to their better creep properties.

Patent document WO 2004/069679 A1 discloses a container with a drop dispenser. The drop dispenser has an insert element with an elongation that acts as mounting aid such that the insert can be inserted into the tube from the proximal end of the tube body and moved through the tube body and its proximal opening into the spout. The insert element comprises a lateral notch that extends into the longitudinal direction and that forms a throttling passage with the inner wall of the spout element of the drop dispenser.

While the drop dispenser disclosed in WO 2004/069679 A1 allows for improved forming of a sequence of singular drops at the spout orifice, liquid might still be dispensed in form of a jet or in form of a drizzle or spray, i.e. uncontrolled, depending on the pressure applied onto the tube body by the user.

SUMMARY OF THE INVENTION

It is an object of the invention to provide an insert for a tube and to provide a tube for controllably dispensing liquid content therefrom as a sequence of regular drops. Dispensing of the liquid as jet or as spray or drizzle should be avoided. It is a further object of the invention to provide an insert for a tube and to provide a tube for dispensing liquid content in the form of drops, wherein the size of the drops is basically independent of the pressure exerted on the tube body by a user.

In order to implement these and still further objects of the invention, which will become more readily apparent as the description proceeds, an insert for a tube is provided, from which liquid content shall be dispensed in the form of drops, in particular as a sequence of drops. The insert is provided with an annular indentation that divides the insert into a proximal part and a distal part in the longitudinal direction. The proximal part is defined as the part that is closer to the orifice of a spout of a tube, into which the insert is to be inserted. The distal part is defined as the part further away from the orifice of the spout. It follows the proximal part after the annular indentation, with the distal part being connected to the proximal part via a shaft formed by the indentation. The shaft extends in the longitudinal direction and is preferably centrally arranged. Both the proximal part and the distal part are preferentially aimed to be entirely inserted into the spout of a tube. In the following the term "proximal" means closer to the orifice of a spout of a tube and the term "distal" means further away from the orifice of the spout, once the insert is mounted in a tube.

The proximal part and the distal part each comprise a notch (also called: groove) on their respective outer walls, the notch extending in the longitudinal direction. I.e. both the proximal and the distal part comprise a lateral notch extending in the longitudinal direction. Alternatively, each notch can be inclined sideways or have the pathway of a spiral, for example. Each notch has preferably a v-shaped profile, but can also be designed to have a u-shaped profile or a different profile, that preferentially can be formed during injection moulding. Each notch can also be formed by cutting away a segment of the respective part of the insert.

The insert is preferably symmetrical with respect to its longitudinal axis. Furthermore, the outer diameter of the proximal part and the outer diameter of the distal part are preferably chosen such that they match the inner diameter of the spout of a tube, into which the insert is to be inserted, such that the proximal part and the distal part sealingly fit into the spout (apart from where the notches run). The proximal part and the distal part are preferentially conical in shape with diameter decreasing toward the orifice of the spout, in particular if the spout is given by a cannula.

The insert preferably comprises a stop element whose diameter is larger than the diameter of the distal part and preferentially also of the proximal part, such that the stop element cannot be pushed into the spout of a tube but rests at its shoulder on the inside. The stop element comprises a recess through which liquid content of the tube body can flow toward the notch of the distal part. The stop element may for example have the shape of an annulus, a hexagonal bar, or a polygonal bar.

The present invention further relates to a tube with a spout that has an orifice for dispensing liquid, a tube shoulder and a tube body, wherein the spout is connected to the tube body via the tube shoulder. An insert according to the invention is inserted into the spout such that its proximal part and its distal part are located inside the spout with their outer walls being in sealing/tight contact with the inner wall of the spout (apart from the notches). I.e. the outer diameter of the proximal part and the outer diameter of the distal part match the inner diameter of the spout. The stop element of the insert abuts on the shoulder of the tube from its inside, such that the stop element cannot be moved into the spout. The tube body consists at least partly of resilient material such that it is bent inward if a user applies pressure to it/squeezes it in order to dispense liquid. The material of the tube or the tube body and/or the tube shoulder may be a laminate. The longitudinal direction is defined as the direction from the distal end of the tube body to the orifice of the spout of the tube. The transverse direction is defined as the direction perpendicular to the longitudinal direction.

The notches of the proximal part and of the distal part of the insert form with the inner wall of the spout a throttling passage for the liquid content. The liquid content contained in the tube body has to pass through this throttling passage before it is dispensed from the orifice of the spout.

The liquid content contained in the tube body may be a liquid pharmaceutical or cosmetic product, for example a serum. A possible pharmaceutical product is liquid for treating eyes, which are dispensed as eye drops if a user exerts pressure onto the tube body. Possible cosmetic serums are for tightening or rejuvenating/regenerating human skin. The employed serums, in particular the employed cosmetic serums, preferably have a viscosity that lies in the range of 1 to 100 mPa·s.

The insert and the tube of the invention have the advantage that by way of the throttling passage the formation of drops is basically independent of the amount of pressure a user applies to the tube body. The throttling passage reduces the flow rate of the pressurized liquid content. The flow rate is even further slowed down by the provision of the indentation between the distal part and the proximal part of the insert, the indentation forming part of the throttling passage and lying between the notches of the distal part and the proximal part. To flow from the notch of the distal part to the notch of the proximal part the liquid has to cross the indentation which further reduces its travelling speed. To even further slow down the flow rate/travelling speed of the liquid the notch of the proximal part and the notch of the distal part are preferably arranged offset to one another in the transverse direction, such that the liquid has to change direction, in particular change direction twice, and speed-reducing turbulences are caused in the indentation.

Hence, with the insert and the tube of the invention dispensing liquid content in the form of drops, in particular as a sequence of regular drops, is facilitated, and dispensing of the liquid content as spray, drizzle, jet or spurt can advantageously be avoided. The insert and the tube of the invention are especially suitable for dispensing viscous liquids, in particular liquids with high viscosity. The length and the width of the throttling passage can be altered by appropriately altering the design of the insert, in particular the design of the notches of the proximal and the distal part and of the indentation. There is no need to change the tube shoulder and the spout of the tube. Thus, through appropriate design of the insert, in particular its proximal part, its distal part and the indentation, the pressure reduction in the liquid can be appropriately adapted to e.g. the viscosity or other properties of a liquid to be dispensed as drops.

According to a preferred embodiment, the insert is provided with a mounting aid that is preferentially arranged at the distal end of the stop element. The mounting aid has preferably the form of a shaft that is at least partly cylindrical or conical. The mounting aid serves as handle or grip for inserting the insert (in particular its proximal and distal parts) into the spout during manufacturing of the tube. The mounting aid is designed such that it does not interfere with the dispensing of the fluid. The mounting aid preferably fits into the bore of a mandrel or can be held by another gripping device.

The proximal end, the distal end, the stop element and the mounting aid of the insert are preferably formed as one piece/integrally, for example by injection moulding.

The insert of the invention has the advantage that it can be inserted into the tube and its spout, respectively, from the distal end of the tube, which simplifies manufacturing. For ease of mounting the insert of the invention is preferably symmetrical along its longitudinal axis, such that mounting is also possible if the insert is not exactly aligned with the spout for insertion. Furthermore, the insert according to the invention is preferably symmetrical along its transverse axis, so that it does not matter which way the insert is held during mounting and mounting is even more facilitated.

As the mounting of the insert is performed in the inside of the tube, additional sealing surfaces toward the outside of the tube (as in case of two-part drop dispensers known in the state of the art) can be avoided. This has for example the advantage that the tube according to the invention can be sterilized with superheated steam to produce a drop-dispending tube which is better sterilized to avoid contamination. After filling the tubes of the invention with liquid content, the tubes are therefor sterilized by preferably about 120 degrees Celsius. This would, however, not be possible if the insert consisted of several separate parts of different materials, i.e. if the insert is not formed as one piece of one material, which would lead to decreased temperature stability and diminished sealing properties.

BRIEF DESCRIPTION OF THE DRAWINGS

Further advantageous features and applications of the invention can be found in the dependent claims as well as in the following description of the drawings illustrating the invention. In the drawings like reference signs designate the same or similar parts throughout the several figures of which:

DESCRIPTION OF THE PREFERRED EMBODIMENTS

Figure 1:
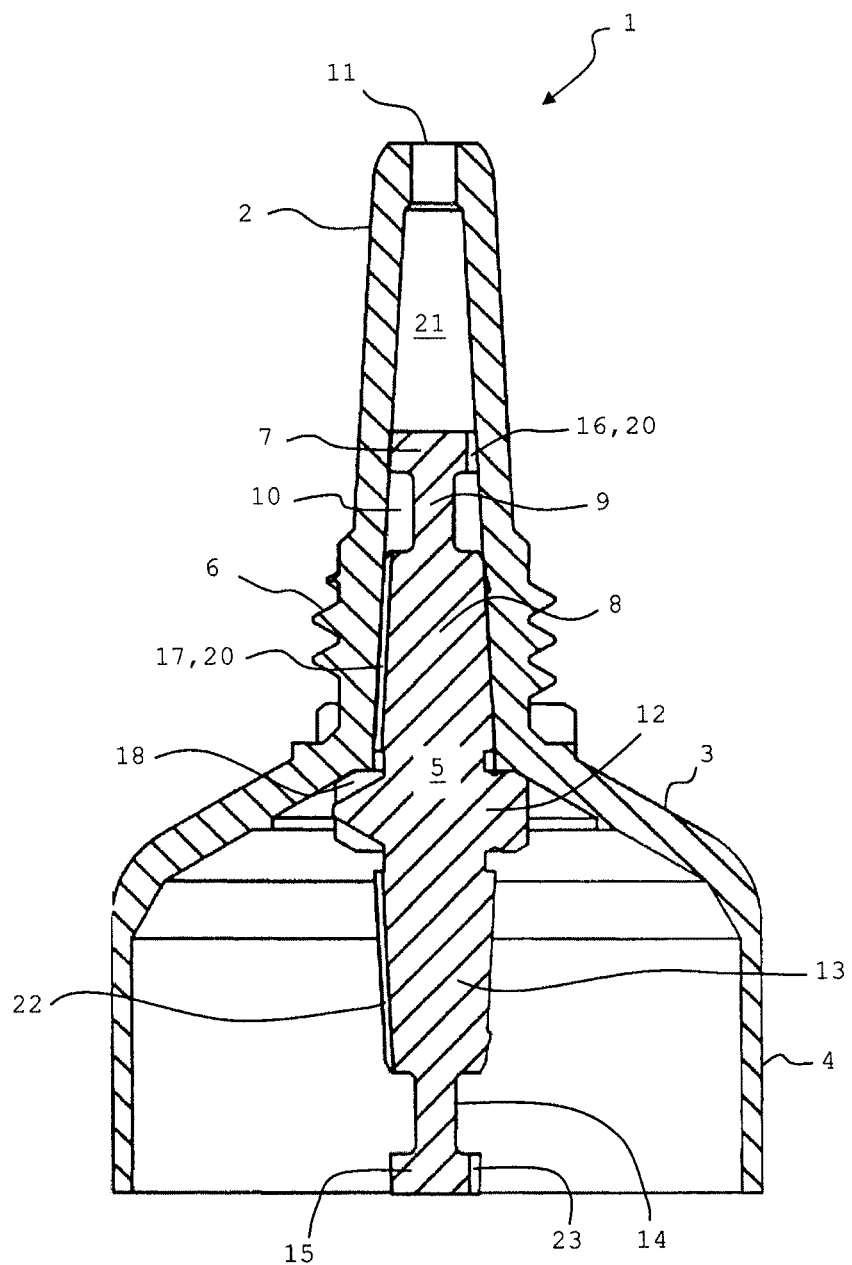
FIG. 1 shows a vertical cross-sectional view of a tube with an insert according to the invention.

FIG. 1 shows a tube 1 according to the invention with an elongated spout 2, a tube shoulder 3, a tube body 4 and an insert 5 according to the invention, the insert 5 being mounted inside the tube 1. For simplicity of presentation the part of the tube body 4 that lies below the insert 5 has been omitted, with "below" referring to the representation in FIG. 1. The spout 2 is preferably formed as cannula for more accurate application of the drops to be dispensed. On its outer wall the spout 2 comprises threads 6 to engage with threads of a cap (not shown) that can be placed onto the spout 2. At its proximal end the spout 2 has an orifice 11 trough which liquid can be dispensed as drops.

Figures 2, 3:
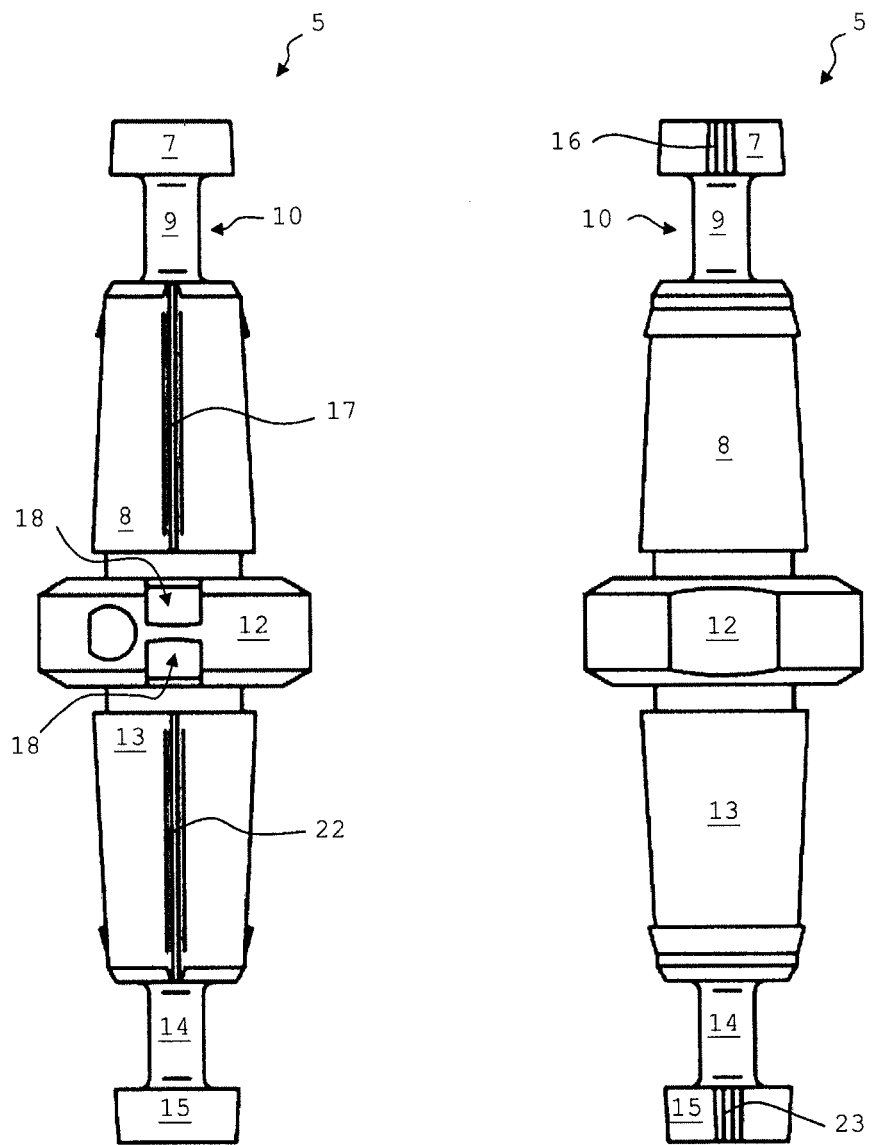
FIG. 2 shows a side view of the insert according to the invention.
FIG. 3 shows a further side view of the insert according to the invention, rotated by 180 degrees with respect to FIG. 2.
Figure 4:
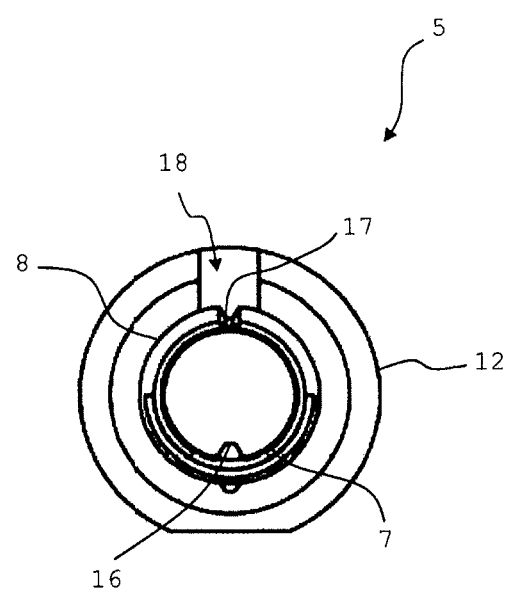
FIG. 4 shows a top view (view from above) of the insert according to the invention.

FIGS. 2 to 4 show the insert 5 of the invention in detail. The insert 5 comprises a proximal part 7 and a distal part 8 that are connected by a centrally arranged shaft 9 that is formed by an annular indentation 10 in the outer wall of the insert 5, i.e. the diameter of the shaft 9 is smaller than the diameter of the proximal part 7 and of the distal part 8. The proximal part 7, the distal part 8 and the shaft 9 are positioned inside the spout 2 of the tube 1 of the invention. The diameter of the proximal part 7 and the diameter of the distal part 8 match the inner diameter of the spout 2 to achieve a tight fit.

The proximal part 7 has preferably a smaller height than the distal part 8, i.e. the extension of the proximal part 7 in the longitudinal direction is smaller than the extension of the distal part 8 in the same direction. Preferably the proximal part 7 is shaped as a disc and performs the function of a baffle plate for the liquid to be dispensed.

At the distal end of the distal part 8 of the insert 5, the insert 5 has a stop element 12, whose diameter is larger than the diameter of the proximal end 7, the diameter of the distal end 8 and the inner diameter of the spout 2. Hence, when inserting the insert 5 coming from the inside of the tube body 4, the stop element 12 abuts on the inner wall of the tube shoulder 3, i.e. the stop element 12 functions as stopping edge. Thus, when mounting the insert 5 inside the tube 1, only its proximal part 7, its distal part 8 and the shaft 9 are moved into the spout.

At the distal end of the stop element 12, the insert 5 preferably comprises a mounting aid 13 in form of a shaft that may be tapered toward the distal end of the tube body 4. This mounting aid 13 serves as handle or grip for inserting the insert 5 mechanically or manually. At its distal end the mounting aid 13 may comprise a shaft 14 of smaller diameter that passes into a disc 15, which—depending on the gripping device used for inserting the insert 5—may be employed for holding and gripping the insert 5.

To allow the liquid content to pass from the tube body 4 to the orifice 11, the proximal part 7 is provided with a notch 16 at its outer wall. Similarly, the distal part 8 is provided with a notch 17 at its outer wall. Furthermore, the stop element 12 is provided with a recess 18, with the recess 18 and the notch 17 of the distal part 8 being connected. The proximal end of the notch 17 and the distal end of the notch 16 are each connected with the indentation 10, i.e. the free space provided by it. A throttling passage 20 for the liquid to be dispensed is formed by the inner wall of the spout 2 and the two notches 16, 17. To allow the liquid to enter this throttling passage 20 the recess 18 is provided in the stop element 12, the free space provided by the recess 18 being limited by the inner wall of the tube shoulder 3.

Thus, the liquid passes from the tube body 4 through the recess 18, the notch 17 of the distal part 8, the indentation 10 and the notch 16 of the proximal part 7 into a delivery passage 20 of the spout 2 and finally leaves the tube 1 through the orifice 11 of the spout 2. The notch 16 of the proximal part 7 and the notch 17 of the distal part 8 are preferentially not aligned with each other but are arranged offset from each other in the transverse direction. Preferably the notches 16 and 17 are arranged at an offset of 180 degrees as shown in the Figures.

The flow ratio and the travelling speed of the liquid are significantly reduced by the throttling passage 20, by the change of flow direction by way of the indentation 10 with the proximal part 7 acting as baffle plate and in particular by the horizontal offset between the notch 16 of the proximal part 7 and the notch 17 of the distal part 8. Through these structural measures dispensing of the liquid as jet, spurt or spray can advantageously be avoided and it can be ensured that the liquid is dispensed as a sequence of drops.

The insert 5 of the invention is preferably not only symmetrical with respect to its longitudinal axis but also with respect to its transverse axis. This facilitates mounting of the insert 5 inside the tube 1 even more, as it does not matter at which end the insert 5 is held or gripped for mounting and inserting. The symmetry with respect to the transverse axis is shown in FIGS. 1 to 3. To achieve symmetry in transverse direction, the dimensions of the mounting aid 13 correspond to the dimensions of the distal part 8 (mirrored along the transverse axis) and the mounting aid 13 also comprises a notch 22 that corresponds to the notch 17 of the distal part 8. Similarly, the dimensions of the shaft 14 correspond to the dimensions of the shaft 9 and the dimensions of the disc 15 correspond to the dimensions of the proximal part 7. Furthermore, the disc 15 is provided with a notch 23 that corresponds to the notch 16 of proximal part 7. Moreover, the stop element 12 is symmetrical with respect to its transverse axis, i.e. the stop element 12 has two identical recesses 18, one on its upper side and one on its lower side (as shown in the FIGS. 1 and 2).

It is to be understood that while certain embodiments of the present invention have been illustrated and described herein, it is not to be limited to the specific embodiments described and shown.

The invention claimed is:

1. A tube with a spout (2), a tube shoulder (3), a tube body (4) and an insert (5) for dispensing liquid content in the form of drops, wherein the insert (5) is provided with an annular indentation (10), the annular indentation (10) dividing the insert into a proximal part (7) and a distal part (8) that are connected by a shaft (9), wherein both the proximal part (7) and the distal part (8) comprise a notch (16; 18) extending in the longitudinal direction on the respective outer wall, wherein the insert (5) comprises a stop element (12) attached to the distal end of the distal part (8), with the diameter of the stop element (12) being larger than the diameter of the distal part (8), wherein the stop element (12) comprises a recess (18), the insert (5) being inserted into the spout (2) such that the stop element (12) of the insert (5) abuts on the tube shoulder (3), characterized in that the outer diameter of the proximal part (7) and the outer diameter of the distal part (8) of the insert (5) match the inner diameter of the spout (2), and that a throttling passage (20) is formed by the notches (16; 17) of the proximal part (7) and of the distal part (8) and by the inner wall of the spout (2), through which liquid content of the tube body (4) must pass before being dispensed.

2. The tube according to claim 1, wherein the liquid content of the tube body (4) is a pharmaceutical product for treating eyes.

3. The tube according to claim 1, wherein the liquid content of the tube body (4) is a serum, in particular a cosmetic serum.

4. The tube according to claim 1, wherein the serum has a viscosity in the range of 1 to 100 mPa·s.

5. The tube according to claim 1, wherein the tube (1) has been sterilized by means of superheated steam.

6. The tube according to claim 1, wherein the notch (16) of the proximal part (7) of the insert (5) and the notch (17) of the distal part (8) of the insert (5) are arranged offset to one another.

7. The tube according claim 1, wherein the proximal part (7) of the insert (5) has a smaller extension in the longitudinal direction than the distal part (8) of the insert (5).

8. The tube according to claim 7, wherein the proximal part (7) of the insert (5) has the shape of a disc.

9. The tube according to claim 1, wherein at the distal end of the stop element (12) of the insert (5) there is provided a mounting aid (13), in particular in form of a shaft.

10. The tube according to claim 9, wherein the mounting aid (13) has a notch (22) on its outer wall, the notch (22) extending in the longitudinal direction.

11. The tube according to claim 10, wherein the insert (5) is designed such that it is symmetrical along its transverse axis.

12. The tube according claim 1, wherein the insert (5) is formed as one piece.

* * * * *

UNITED STATES PATENT AND TRADEMARK OFFICE
CERTIFICATE OF CORRECTION

PATENT NO. : 9,090,384 B2  
APPLICATION NO. : 14/359955  
DATED : July 28, 2015  
INVENTOR(S) : Andreas Geiger et al.

Page 1 of 1

It is certified that error appears in the above-identified patent and that said Letters Patent is hereby corrected as shown below:

In The Claims

Claim 4, column 7, line 3: delete "claim 1" and insert -- claim 3 --.

Signed and Sealed this  
Fifteenth Day of March, 2016

Michelle K. Lee  
*Director of the United States Patent and Trademark Office*